May 9, 1972 R. MILLAY Plant Pat. 3,153
STRAWBERRY PLANT
Filed April 6, 1970
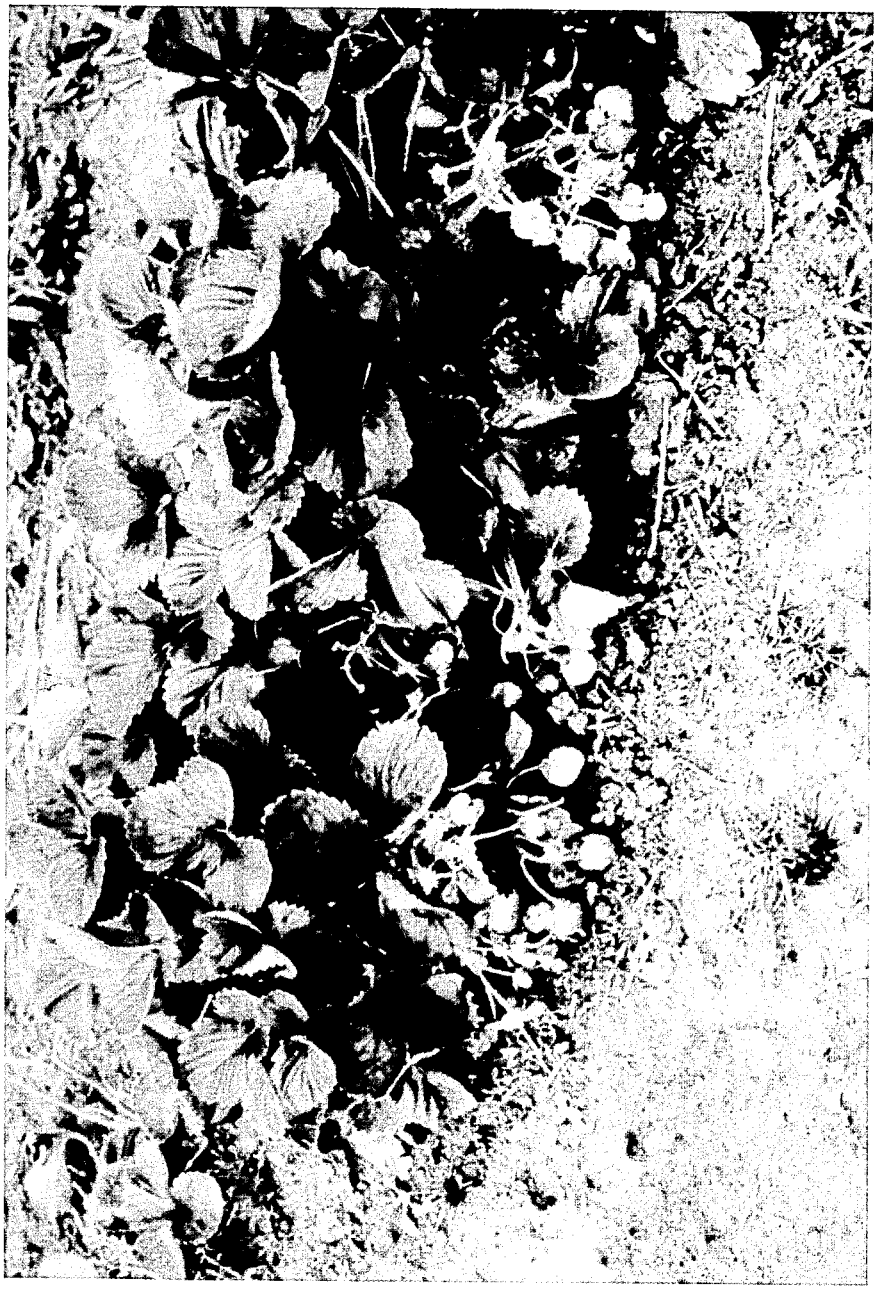
Inventor.
Ruth Millay
By: Robb & Robb
Attorneys.

United States Patent Office

Plant Pat. 3,153

Patented May 9, 1972

3,153
STRAWBERRY PLANT

Ruth Millay, Portland, Maine, assignor to June F. Littlefield, Lewiston, Esther Lavoie, Lisbon Falls, and Lorna A. Young, Portland, Maine, fractional part interest to each

Filed Apr. 6, 1970, Ser. No. 26,175
Int. Cl. A01h *5/03*
U.S. Cl. Plt.—49 1 Claim

The present invention relates to a new and distinct variety of strawberry plant which was discovered by me as a cultivated sport or mutation of the strawberry variety known as "Red Rich" (Plant Patent No. 993—expired), said discovery having been made in my garden on my farm property located at Bowdoinham, Maine.

At the time of my discovery, I was growing in my garden aforesaid plants of "Red Rich" which I had purchased from a reputable commercial nursery in New York State. These plants produced very few runners (mostly only 1 or 2 per plant, and, some none at all) and all of the runners were very short (12 or 13 inches long) and curved around the plant. These runners set runner plants only 2 or 3 inches apart and produced fruit primarily in the spring and to a lesser extent in the fall.

During the growing of my "Red Rich" plants aforesaid, my attention was attracted to one particular plant which had only 1 runner and which had set 7 runner plants, the sixth plant of which had produced 4 runners, each of which was about 20 to 24 inches long in the month of May when I first noticed the same while still attached to the "mother" plant. This was unusual since no other plants had any runners at that time, so I carefully preserved the same and found that the runners continued to grow exceptionally long, straight and stiff, and reached a length of approximately 6 feet before they froze in the late fall, while setting many new runner plants during the first growing season. From the original runner plant produced by the "mother" plant referred to in the foregoing, and from the runner plants derived therefrom and which in turn sent out more runners, I obtained many new plants which I saved and set out in my garden aforesaid the following spring, and of these, each plant produced no less than 15 runners each, with most having from 18 to 24 runners, and each runner grew 6 feet long before freezing at the end of the season. All plants grown from plants set out by these long runner plants grew to a size substantially larger than the plants of "Red Rich" which were growing in the same garden and under the same conditions. Moreover, my new runner plants bore fruit more heavily and set buds continuously without pause. In addition to bearing fruit more continuously and more heavily the fruit of my new plants had a superior flavor as compared with the fruit of "Red Rich."

As the result of my prolonged observations and tests of my new strawberry plant and its progeny, which I have asexually reproduced by rooted runner plants derived therefrom, I am convinced that I have discovered and developed a new and distinct strawberry variety which is distinguished from and superior to the variety "Red Rich" and all other varieties of which I am aware, as evidenced by the following unique combination of characteristics which are outstanding therein:

(1) A general resemblance to the "Red Rich" strawberry variety, but having
(2) A habit of producing longer, straighter, stiffer and more numerous runners ranging up to six feet in length before freezing weather;
(3) A substantially larger plant size;
(4) A more continuous everbearing habit without pause between spring and fall seasons;
(5) Heavier fruit production; and
(6) A superior fruit flavor.

The accompanying drawing shows a typical specimen plant of my new strawberry variety, with the foliage and fruit in different stages of development and depicted in color.

Although the details of my new sport or mutation, except for the characteristics and distinctions referred to in the foregoing, are generally similar to those of the strawberry variety known as "Red Rich" as described in Plant Patent 993, to which reference may be readily had, the following brief description is given for convenience, with color terms of ordinary dictionary significance being used in view of the lack of any significant color distinctiveness:

Locality where grown and observed: Bowdoinham, Maine.
Dates of first and last pickings: Last part of June and about October 21, respectively.
Plant:
- *Growth.*—Vigorous; up to 50% larger than plants of "Red Rich" grown under identical conditions on my farm in Maine.
- *Root.*—Vigorous.
- *Crown.*—Many; large size.
- *Leaves.*—Many; large size; usually trifoliate, but sometimes 4 or 5 leaflets to each stem. Petiole—long; stout. Color—dark green. Serrations—regular. Leaflets—upper surface—glossy. Color—dark green. Lower surface—color—dark green.
- *Runners.*—Appear during fruiting; numerous; long (up to 6 feet before freezing weather); straight; stocky; stiff.
- *Flower stems.*—Long; some inflorescences exposed and some protected by foliage.

Bloom: Early.
- *Date of first bloom.*—Usually begins bloom as soon as snow is gone.
- *Date of full bloom.*—In June.
- *Flowers.*—Many; perfect; frequent double stalks of blooms; flower stalks thicker, up to 50% taller, and more numerous (from 25 to 40 stalks per plant) than those of "Red Rich."

Fruiting stems: Long; stout; radical equals main truss; many branches per truss.
Soil where grown: Clayey; poorly drained.
Culture: Frequent cultivation, but never sprayed.
Disease and insect resistance: Both plant and fruit have good resistance to usual strawberry diseases and insects as determined by comparison with other varieties grown under the same conditions at Bowdoinham, Maine.
Drought resistance: Good; grows and bears well even in dry weather.
Frost resistance: Good; runners continue to grow and plants continue to bear fruit until ground freezes.
Fruit: More abundant than "Red Rich"; can be picked daily from July to hard freeze in October; average yield at least 1 quart per month per plant.
- *Condition when described.*—Prime.
- *Size.*—Variable; usually large; constant throughout. Average length—from about 1½ inches to 2 inches. Average breadth—from about 1 inch to 2 inches.
- *Form.*—Usually wedge-shaped, but some are short and nearly round.
- *Stems.*—Radical—stout; long. Main truss—stout.
- *Calyx.*—Even with surface; green after picking. Upper surface—color—light green. Lower surface—color—light green. Segments—oval form.
- *Surface*—Glossy. Color—dark red.
- *Seeds.*—Inconspicuous; small; even with surface; medium number of lower seeds on berries.
- *Core.*—Mostly solid. Color—dark red.

*Flesh.*—Juicy. Color—dark red. Texture—firm; fine.

*Flavor.*—Rich; very sweet (even sweeter than "Red Rich" and very delicious without the addition of sugar); aromatic.

*Quality.*—Best.

Shipping quality—good.

Keeping quality—very good; excellent for freezing and do not become mushy when thawed for eating, and retain sweetness without adding sugar.

*Use.*—Dessert.

General observations: The current leading commercial strawberry variety is "Ozark Beauty" (unpatented). In comparison therewith, my new variety bears fruit more abundantly and its fruit has less prominent seeds and is much darker red in color. The leaves of my new variety are darker green in color and the runner plants set farther apart. The plants of my new variety have more crowns, larger, longer and more numerous roots, and the plants produce more blooms, and the bloom stems are stouter and longer. My new variety is also superior to "Geneva" (unpatented) since it bears fruit more abundantly and for longer periods of time, and the fruit is darker colored.

I claim:

1. A new and distinct variety of strawberry plant, substantially as herein shown and described, characterized by the unique combination of a general resemblance to the "Red Rich" strawberry variety, but having a habit of producing longer, straighter, stiffer and more numerous runners ranging up to six feet in length before freezing weather, a substantially larger plant size, a more continuous everbearing habit without pause between spring and fall seasons, heavier fruit production, and a superior fruit flavor.

No references cited.

ROBERT E. BAGWILL, Primary Examiner